United States Patent [19]

Ibrahim et al.

[11] Patent Number: 5,127,919
[45] Date of Patent: Jul. 7, 1992

[54] WOVEN VASCULAR GRAFT

[75] Inventors: Ibrahim M. Ibrahim, Closter; Indu Kapadia, Denville, both of N.J.

[73] Assignee: Vascutec Corporation, N.J.

[21] Appl. No.: 644,674

[22] Filed: Jan. 22, 1991

Related U.S. Application Data

[63] Continuation of Ser. No. 284,417, Dec. 14, 1988, abandoned.

[51] Int. Cl.⁵ .............................................. A61F 2/06
[52] U.S. Cl. ........................................ 623/1; 623/66; 139/387 R; 139/383 R
[58] Field of Search ............................ 623/1, 12, 66; 139/387 R, 383 R

[56] References Cited

U.S. PATENT DOCUMENTS

| 955,541 | 4/1910 | Petersen . | |
|---|---|---|---|
| 1,139,467 | 5/1915 | Cole . | |
| 1,634,412 | 7/1927 | Fefel | 139/383 R |
| 2,986,171 | 5/1961 | Eisen | 139/383 R |
| 3,283,389 | 11/1966 | Nisbet et al. | 139/383 R |
| 3,878,565 | 4/1975 | Sauvage . | |
| 3,945,052 | 3/1976 | Liebig | 623/1 |
| 3,986,828 | 10/1976 | Hoffman, Jr. et al. | 8/115.5 |
| 4,047,252 | 9/1977 | Liebig . | |
| 4,282,011 | 8/1981 | Terpay . | |
| 4,517,687 | 5/1985 | Liebig . | |
| 4,530,113 | 7/1985 | Matterson . | |
| 4,816,028 | 3/1989 | Kapadia et al. | 623/1 |

FOREIGN PATENT DOCUMENTS 0834403 11/1938 France .
0825183 12/1959 United Kingdom .

OTHER PUBLICATIONS

Textile Encyclopedia, Entries for "Jacquard", pp. 303-306 (Exh. B to Amendment filed Nov. 12, 1991).
Excerpt from a volume on Textiles, Section on the Jacquared Loom, p. 338 (Exh. C to Amendment filed Nov. 12, 1991).
Excerpt from a volume on Weaving, showing Jacquard Loom, pp. 134, 136 and 137, (Exhibit D to Amendment filed Nov. 12, 1991).
Textile Dictionary, Chapter on "Weaving", pp. 332, (Exh. E to Amendment filed Nov. 12, 1991).
Dictionary of Textile Terms, Enter for "Jacquard", p. 556 (Exh. F to Amendment filed Nov. 12, 1991).
Watson's Textile Design and Colour, Elementary Weaves and Figured Fabrics, 7th Edition, Chapter 11 entitled "Elements of Jacquard Shedding", p. 178 (Exh. G to Amendment filed Nov. 12, 1991).
Textile Dictionary, Entry for "Jacquard", pp. 313-314, (Exh. H to Amendment filed Nov. 12, 1991).
Textiles: Fiber to Fabric, Chapter 5 on "Weaving" pp. 113-115 (Exh. I to Amendment filed Nov. 12, 1991).
Textile Progress vol. 15 (1986) No. 3, Manchester, Great Britain; pp. 1-30 "Vascular Grafts: Textile Structures and Their Performance".

Primary Examiner—Randall L. Green
Assistant Examiner—Paul Prebilic
Attorney, Agent, or Firm—Rosen, Dainow & Jacobs

[57] ABSTRACT

A vascular graft prosthesis of woven synthetic yarn where selected fill threads are woven into S-shaped lock elements about selected warp threads to provide a tubular fabric that resists fraying when cut at an oblique angle.

16 Claims, 8 Drawing Sheets

|    | W1 | W2 | W3 | W4 | W5 | W6 |
|----|----|----|----|----|----|----|
| F9 | X  | X  | O  |    | X  |    |
| F8 | O  | X  | X  | X  | O  | O  |
| F7 | X  | X  | O  | X  | X  | X  |
| F6 | O  | O  | X  | O  | O  | X  |
| F5 | X  | X  | O  | X  | X  | X  |
| F4 | O  | X  | X  | X  | O  | O  |
| F  |    | X  | O  | X  | X  | X → F3 |
| F  | O  | X  |    |    |    |    |
| F3 | X  | X  | O  |    |    |    |
| F2 | O  | X  | X  | O  | O  | X  |
| F1 | X  | X  | O  | X  | X  | X  |

WOVEN VASCULAR GRAFT

This application is a continuation of application Ser. No. 07/284,417, filed Dec. 14, 1988 now abandoned.

BACKGROUND OF THE INVENTION

This invention is in the field of vascular grafts made of synthetic fibers that may be used in a variety of vascular surgical procedures. Particular interest herein is to grafts used to replace occluded portions of arteriosclerotic vessels or used to form new blood pathways in a vascular reconstruction procedures as generally disclosed in U.S. Pat. Nos. 4,517,687, 4,047,252, 4,530,133, and 3,878,565 and in applicants' co-pending application Ser. No. 068,662 which issued on Mar. 28, 1989 as U.S. Pat. No. 4,816,028.

There are basically three kinds of prior art grafts, namely extruded, knitted and woven. Extruded grafts have the desirable characteristics of being generally strong and nonporous which precludes subsequent hemorrhaging. Unfortunately, this absence of porosity prevents tissue ingrowth following implantation, such ingrowth being considered desirable. Also these grafts are relatively stiff and nonconforming and thus are difficult to handle, suture and implant.

Knitted grafts have certain advantages over extruded grafts, namely porosity, flexibility, softness and a structure adaptable to have a velour type outer surface. Accordingly, they conform easily to blood vessels, which reduces surgeon's and patient's time in the operating room; the porosity and velour surfaces allow considerable endotheliazation (tissue ingrowth). The principal disadvantage of knitted grafts is that the porosity is so great, hemorrhaging will occur unless the graft is preclotted.

Preclotting is a separate step whereby the graft is immersed for about fifteen minutes in a quantity of about 100-150 ccs. of the patient's own blood, after which the graft is allowed to stand for clotting to occur. Preclotting substantially prevents hemorrhaging, while allowing subsequent tissue ingrowth; however sometimes preclotting is not permissible, as where the patient has been anti-coagulated or has bleeding diathesis. In these cases a knit graft requiring preclotting cannot be used. A further negative consideration about knitted grafts is that they dilate and stretch more than other types.

Another known knitted graft is coated in manufacture with albumin to prevent initial bleeding following implantation. Other prospective coated grafts will use collagen or gelatin for the same purpose. The albumin coating obviates the necessity for typical preclotting during surgery; however, such coating renders the tubular graft stiffer and more difficult to handle during implantation. Also such a coated product is considerably more expensive than a simple woven graft. A further disadvantage of an albumin-coated graft is that it must be prepackaged in saline.

Woven grafts have certain advantages over both extruded and knitted grafts. In woven grafts porosity is lower so that preclotting is not required. Woven grafts have the disadvantage of being relatively stiffer and less conforming than knit grafts, and thus they are more difficult and time consuming for surgeons to use. A further disadvantage with known woven grafts is a tendency for the end edge of a tubular graft to fray when cut. Tubular grafts may be cut perpendicular to the axis of the tube producing a generally round end opening or cut oblique to the axis producing a generally oval end opening. With a perpendicular cut there is a tendency for fraying of weft or pick threads since they are exposed at the end of the graft. Such fraying has been substantially reduced by the use of periodic double leno warp threads within the overall weave as described in applicants' copending application, Ser. No. 068.662 which issued as U.S. Pat. No. 4,816,028. Oblique cuts of the graft are often preferred to perpendicular cuts because the resulting greater cut surface area to be sutured adds security; also, the oblique junction avoids an abrupt direction change and thus permits smoother blood flow. Unfortunately, oblique cut graft ends have a tendency for fraying of both warp and pick threads for which the double leno weave is not a fully satisfactory solution. Any fraying of the cut edge not only causes delays during surgery, it may render the graft unsafe and unusable.

The above description of prior art grafts shows some of the numerous parameters considered in the selection of vascular grafts. Additional factors include tissue compatibility, nonthrombogenicity of the surface, deterioration of the graft with time, resistance to infection and resistance to kinking at the joints of the patient.

Typically in the manufacture of both knitted and woven tubular grafts, after the tubular body is formed it is crimped to form circumferential corrugations or ribs that provide strength and resilence against kinking and collapsing of the tube or narrowing of the lumen from bending or twisting. Known woven grafts often use a polyester yarn such as Dacron ® (polyethylene terephthalate) yarn, Type 56 made by E. I. Dupont Corp. Such yarn has been designated 40 denier/27 or 70 denier/34, where 40 denier/27 or 40d/27, for example, represents 40 grams of weight per 9000 meters of yarn and comprises 27 filaments, or 1.48 denier per filament. Dacron ® is a registered trademark of E. I. Dupont for polyester yarn. The selection of 40 d/27 yarn in single or double ply as the standard of the industry has been dictated by what was available on the market and what has been approved by the F.D.A. Prior patents referred to above describe more fully this standard yarn, which may also be texturized in a standard way. i.e. false twisting the yarn fibers at a spindle speed of about 250,000 rpm, under 8 to 15 grams of tension at about 450°F. Double ply yarns cited above are formed by twisting together two texturized yarns at a twist of about one half turn per inch.

The weaving of arterial grafts is done on known weaving apparatus with a matrix of warp threads through which are woven weft or fill threads. By incorporating a twill or velour weave, velour loops are produced in certain warp threads on the inner and/or outer surfaces of the woven fabric. As is known, these twill threads are preshrunk, so that upon the subsequent shrinking of the completed woven graft tube made of otherwise unshrunk yarn, all threads will shrink except the velour ones which will extend outward from the surface as loops adapted to receive tissue ingrowth.

In view of the above-described function parameters and the differences between the various prior art grafts, compromises in characteristics are required with each selection. More specifically, if one wishes softness and pliability and porosity, the choice must be a knit graft with the required preclotting.

In applicants' co-pending application, Ser. No. 068,662, which issued as U.S. Pat. No. 4,816,028, an invention was disclosed that provided a graft of a woven fabric with softness and pliability of a knit fabric and the low porosity of prior art woven fabric, thus avoiding the high porosity and preclotting requirement of knit and the stiffness of prior woven grafts. Such new fabric utilized various weave patterns (particularly double lenos in place of certain warp threads), where each leno consists of a pair of warp threads twisted or crossed one over the other between successive fill threads, and a double leno consists of a pair of lenos. Between sets of lenos is a set of plain/twill threads, each set comprising, for example, four warp threads alternating as plain, twill, plain, twill. Typically, a twill designated "3/1", means the fabric is woven so that the twill thread lies "over" three successive fill threads, then "under" the next fill, then over the next three, etc. The alternating plain threads designated "1/1" means simply "over" one fill, "under" the next fill, over the next, and so on.

The lenos are effective in reducing fraying or unraveling of a graft, particularly where the cut is perpendicular to the tubular axis of the graft. As discussed above, these lenos, while helpful, do not provide a fully satisfactory solution for extreme oblique cuts at the tubular end of a woven graft. Even a small amount of fraying is bothersome to a surgeon; significant fraying causes serious concern for the security and patency of the suture line. Such concern has led to the present invention of a new and substantially different and better weave pattern for the fabric of the graft, regardless of what combination of plain, twill and/or leno threads it has, as discussed below.

SUMMARY OF THE INVENTION

The new vascular graft of this invention provides a combination of critical advantages that have been previously available only partially with knit grafts and partially with woven grafts and partially with extruded grafts. More particularly the new graft has the low porosity of woven grafts, the softness and pliability of knit grafts, and the non-fraying feature of extruded grafts. The new invention incorporates a totally new weave pattern into the woven fabric, regardless of whether such fabric is a plain weave, or a plain/twill matrix, or a plain/twill matrix with alternating single or double lenos, or other matrices or combinations of the above as disclosed in applicants' co-pending application. More specifically in this new invention, we have added a plurality of lock weave elements which are distributed through the fabric matrix pursuant to a specific weaving technique. Each locking element constitutes a fill thread formed into a double reversed configuration about one or more warp threads, said fill thread then continuing in its original direction as a standard fill traversing warp threads until the fill is formed into another similar lock element about another one or more warp threads. Typically, lock elements are spaced apart in the transverse or fill direction by at least one unlocked warp thread.

Each locking element creates a build-up or bulge of two extra lines of fill thread in the warp direction. The extra lines of each lock element generate more fabric in the axial or warp thread direction at each site where a lock element occurs. Inbetween each two lock elements formed by a single fill thread would be a small space, however, with subsequent fill threads in the axial direction, the next fill thread that includes a lock stitch has such stitch positioned generally transversely between the spaced apart lock stitches of earlier fill thread. The two-thread build-up from each new lock element transversely intermediate the prior build-ups tends to even out the axial bulges in the weave, so that the successive fill threads tend to lie generally flat and perpendicular to the warp threads.

These new fabrics may be woven on Dobby or Jacquard type looms such as known in the art for creating flat or tubular fabric of traditional weave patterns. In the new weave each lock element is created by moving the beddles of the loom as required to create open sheds for the shuttle to pass with resulting fill thread forming the double reverse or S-shaped lock element about the selected warp threads. After the lock element to be formed by one fill thread is so formed, then the exposed fill is beaten by a comb at which time the fabric is advanced through the loom, and the warp matrix is ready to a next fill thread.

In the preferred embodiment of this new fabric lock elements may be distributed in the following patterns:

a) for any single fill thread the lock elements in the fill direction are separated by at least one warp thread:

b) successive fill threads in the warp direction that include lock elements are separated by at least three successive standard fill threads that do not include lock elements:

c) successive lock elements in the transverse direction formed by different but successive fill threads are separated by at least one warp thread; and d) each lock element locks on at least one warp thread and preferably on no more than three warp threads.

In a loom's basic matrix setup, the warp threads may comprise many possible arrangements, where "plain 1/1" or "1/1" means over one, under one, etc., "twill 3/1", or "3/1", means over 3, under 1, etc. to create a velour; "leno" means a pair of crossed warp threads, and "double leno" means two pairs of crossed threads.

The warp matrix may consist of the following or other combinations which are repeated:

| a) | 1/1 3/1 | | | | | |
| b) | 1/1 3/1 | double leno | | | | |
| c) | 1/1 3/1 | 1/1 | 3/1 | double leno | | |
| d) | 1/1 3/1 | 1/1 | 3/1 | 1/1 | 3/1 | double leno |
| e) | 1/1 3/1 | 1/1 | 3/1 | leno | leno | leno |
| f) | 1/1 3/1 | 1/1 | 3/1 | 1/1 | 3/1 | double leno |
| g) | 1/1 3/1 | 1/1 | 3/1 | 1/1 | 3/1 | leno leno leno |

BRIEF SUMMARY OF THE DRAWINGS

FIG. 6 is a fragmentary schematic showing a lock stitch in a plain 1/1 weave pattern;

FIG. 8 is a fragmentary schematic plan view showing a lock stitch in a 1/1, 3/1 plain, twill weave pattern where each successive 3/1 twill is advanced by two picks;

FIG. 9 is a fragmentary schematic plan view showing a lock stitch in a 1/1, 3/1 plain, twill weave pattern where each successive 3/1 twill is advanced by three picks;

FIG. 11 is a fragmentary schematic plan view in enlarged scale showing a lock stitch in a 1/1, 3/1, 1/1, 3/1 plain, parallel twill double leno weave pattern where the 3/1 twill does not advance.

DETAILED DESCRIPTION OF THE PREFERRED EMBODIMENTS

Figure 1:
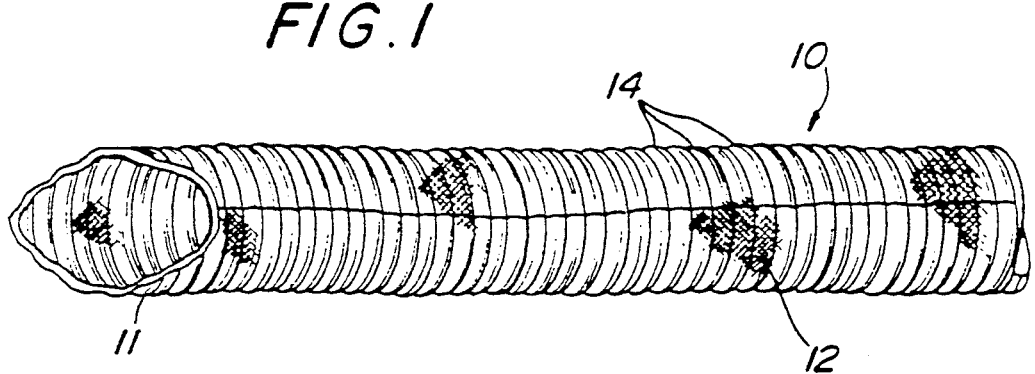
FIG. 1 is a fragmentary perspective view of a vascular graft of the new invention with an oblique cut end.
Figure 2:
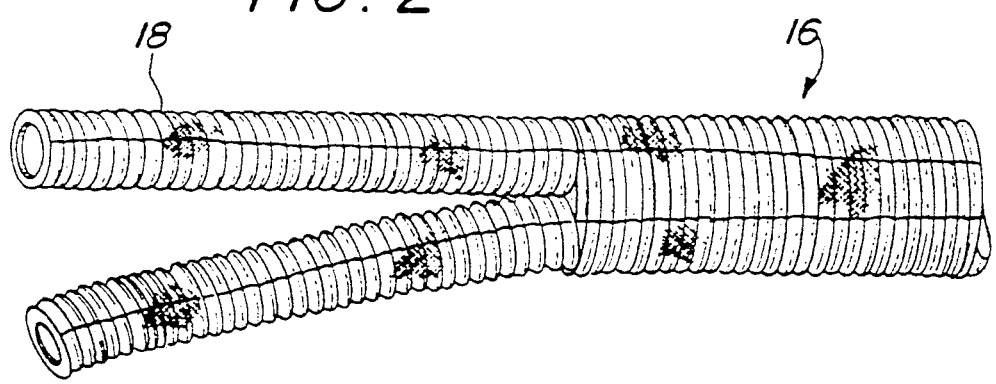
FIG. 2 is a fragmentary perspective view of a bifurcated vascular graft similar to FIG. 1 without oblique cut ends.
Figure 3:
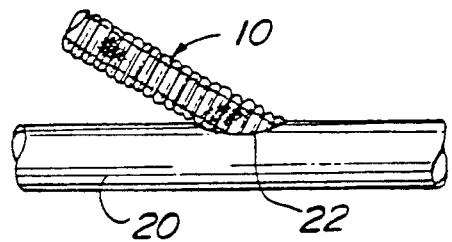
FIG. 3 is a fragmentary perspective view of a graft with an oblique cut end sutured to a patient's blood vessel.

FIG. 1 shows a segment of the new vascular graft 10 with its left end 11 cut at an oblique angle. The graft is formed of a woven fabric 12. Along the length of the graft are ribs 14 which are formed by permanently crimping the tube after it is woven. FIG. 2 shows a second embodiment 16 of the new graft which has its left end bifurcated into two legs 18. FIG. 3 shows the segment of the graft 10 sutured onto a patient's blood vessel 20 along a sutured line 22. Before this attachment, the graft end 11 is out at the oblique angle as shown in FIG. 1, and a corresponding opening is created in the vessel 22 for a good fit at the time of implantation of the new graft.

Figure 4:
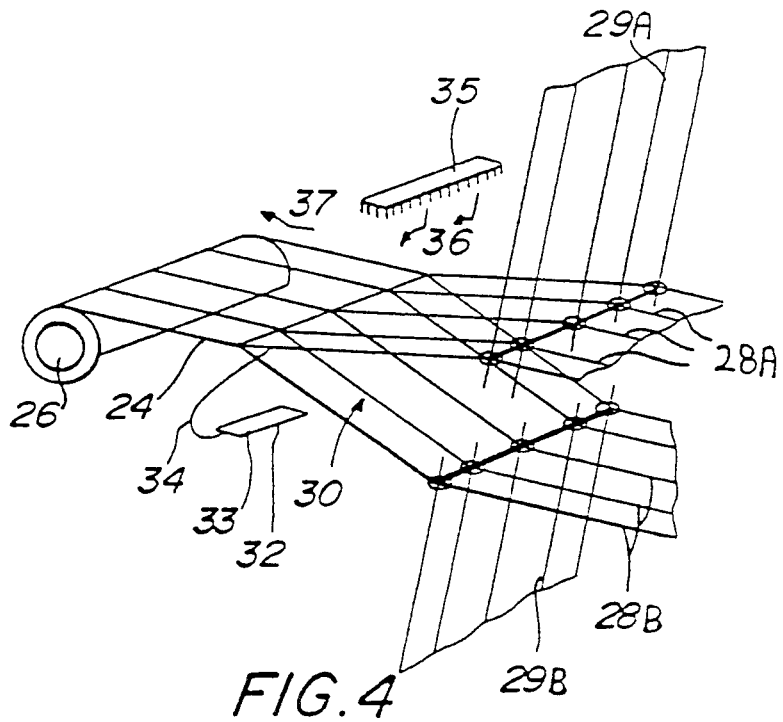
FIG. 4 is a fragmentary perspective schematic view of a weaving loom.

FIG. 4 shows a partial schematic representation of certain weaving loom parts. In this figure the woven fabric 24 is wound onto a take-up roller 26 which revolves counter clockwise. The fabric is created by transverse fill threads woven through warp threads represented by threads 28A and 28B which are shown as separated upward and downward respectively by heddles 29A and 29B. The warp threads when separated in this manner create a shed 30 through which the shuttle 32 is inserted and passed. The shuttle contains a spool of yarn 33 which of course extends from the previously woven fill line 34. A comb 35 periodically is moved downward and rearward in a direction of arrows 36 to beat the last woven fill thread against the existing fabric. Further appropriate elements not shown cause the fabric to be moved rearward in the direction of 37 and onto the take-up roller 26 with each completed weave line. To create various plain, twill, and leno weave patterns, the heddles 29A and 29B are selectively moved so that the shuttle will bring a fill thread to only the particular warp threads selected for each particular line.

Figure 5:
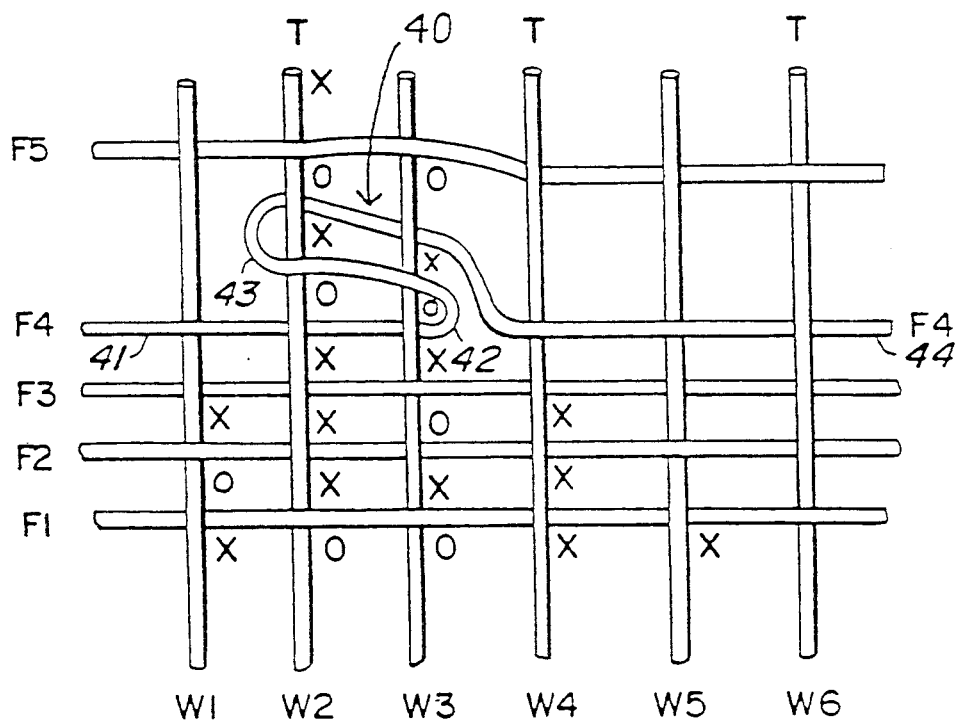
FIG. 5 is a fragmentary plan view in enlarged scale showing; a lock stitch in a plain, twill, plain, twill weave pattern.

FIG. 5 shows a small segment of a weave pattern greatly enlarged where warp threads W1, W2, W3, W4, W5 and W6 are shown in the vertical axes. Fill threads are indicated by F1, F2, F3, F4, and F5 in the horizontal direction. In this particular weave pattern, the W1 thread is a basic plain 1/1 thread in that it goes over F1, under F2, over F3, under F4, and over F5. Warp threads W2, W4 and W6 are all 3/1 twill threads in that each one extends under one fill, over the next three, and under the one. See for example, the W6 warp thread which is under F1, and then over F2, F3, and F4, and then under F5. Such a twill weave ultimately produces a velour loop on the surface where the over three portion lies. The W2 warp thread is also a 3/1 twill; however, it participates in the lock element or lock stitch 40. As shown this lock stitch is created by fill thread F4 which extends over W1 under W2 and under W3. At this point F4 is reversed backward to go over W3 and W2 where it is reversed again to go under W2 and under W3, and thence to continue over W4 over W5 and under W6. When fill thread F4 completes its stroke in the rightward direction, the loom's comb 35 as shown in FIG. 4 comes down and beats this thread against its previous fabric matrix so that the lock stitch is substantially tight. A completed fabric formed into the vascular graft will have many of these type lock elements distributed throughout the weave matrix. Accordingly, when the graft is cut, particularly when cut in an oblique angle for subsequent junction with a patient's blood vessel the various lock elements will contribute greatly toward reducing or preventing fraying of the adjacent warp and fill threads. As seen in the lock element specimen of FIG. 5, the various warp threads maintain their basic plain twill pattern of 1/1, 3/1 construction even through the lock element.

During the actual creation of the lock element in FIG. 5, a shuttle carrying the F4 fill thread will first move to the right as shown from points 41-42. The comb then beats that line even though the fabric already created is not advanced by the take-up mechanism. Next the shuttle goes to the rearward direction from points 42-43, during which time the relevant warp threads are moved upward or downward to create the appropriate shed as generally indicated in FIG. 4. Then the comb beats this segment of fill thread F4 again without the take-up mechanism moving the fabric. Next the shuttle moves to the right from point 43 to point 44 during which time the appropriate warp threads are moved up and down as generally discussed before to create the appropriate sheds and to made sure that warp thread W2 for example is up while the shuttle goes under it, whereby the fill thread is wound about warp W2 and achieves the lock thereon. After the shuttle has moved to point 44 or to the extreme rightside and completed its stroke, the comb beats once again, and this time the take-up mechanism causes the fabric to move by one step to get ready for the next shed opening and the next stroke of the shuttle.

As seen in FIG. 5 fill thread F4 locks about two adjacent warp threads W2 and W3. F4 has an initial fill direction of left to right; F4 then loops about W3, the second of the adjacent warp threads and extends in the opposite direction traversing said W2 and W3 threads; F4 then loops about W2, the first of said adjacent warps and extends back in the original fill direction traversing W2 and W3. The locked adjacent warps comprise at least one, or two, three or four threads. The portion of the fill thread that forms the lock element may begin below or under a warp thread and loop over it in the first reversal, or the fill may begin over the warp and loop under it. In either case, the portion of the reversed fill that extends in the direction opposite the initial fill direction traverses the relevant warp threads either above them or below them, and then reverses and is looped about the first of the relevant warps. After the second reversal, the fill traverses the relevant warps either above them or below them as it extends in the original fill direction. For the fill to extend either above or below the relevant warps is an obvious consequence since the shed created in the loom operation allows the shuttle and associated fill thread to traverse all the relevant warps, either above them or below them, in a single pass.

FIGS. 6, 7, 8, and 9 illustrate schematically four variations of weave patterns, all of which utilize the lock stitch as described above. In these four figures and as partially shown in FIG. 5, every "X" represents an intersection of warp and fill threads where the warp thread is over the fill thread. Correspondingly, each "O" represents and intersection of a warp thread and a fill thread where the warp thread is "under" the fill. Accordingly, a plain 1/1 warp thread weave will have the warp thread over one fill thread, under the next, over the next, under the next etc., and this will appear on the figure as a line of X, O, X, O, etc. Where the warp thread is woven in a twill pattern, such thread will be under one fill over the next three fills, and will be shown by a line of O, X, X, X, O, X, X, X, O, etc.

Figure 6:
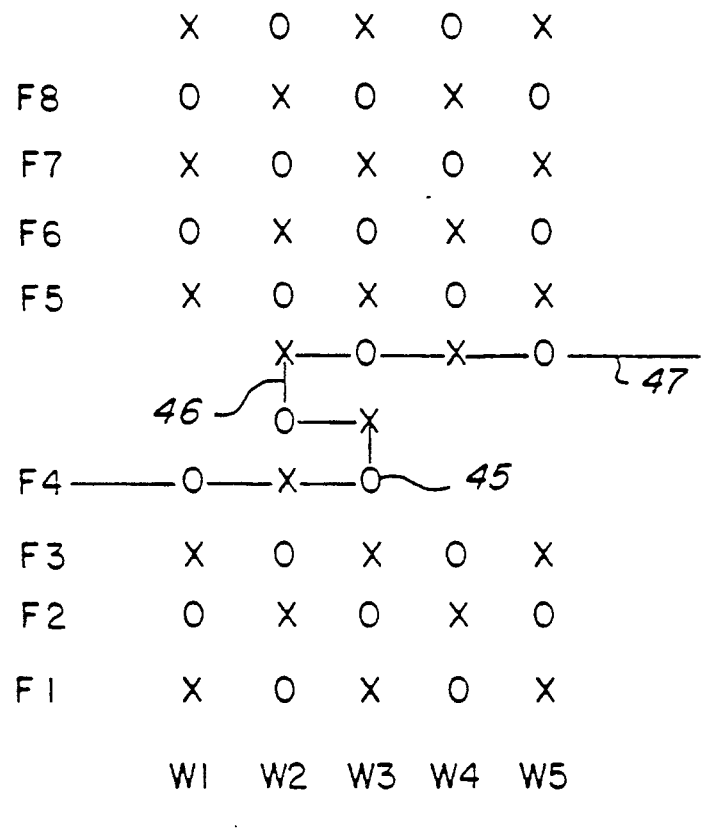

In FIG. 6 the weave pattern is a plain 1/1 weave throughout so that each of the warp threads W1, W2, W3 etc. is shown as an X, O, X, O pattern. The lock stitch in FIG. 6 is formed by fill thread F4 which begins its reverse at W3 indicated by reference numeral 45 and then goes backward to W2 where it has a second reverse indicated by reference numeral 46, after which it continues a forward direction to point 47 where it continues the original F4 stroke.

These lock elements are distributed throughout the weave at a certain frequency and a certain spacing from each other as will be described below. In an alternate form, this lock stitch arrangement would be done only near the end portion of the graft which would be cut at an oblique angle, because the remaining length is not cut and thus would not be exposed to unraveling. The lock elements typically would be spaced apart from each other by at least one warp thread and preferably by two or three. As shown in FIG. 6 the lock element occurs on warp threads W3 and W2. In order to provide a space of at least one warp thread before the next locking element, this means that a subsequent lock would not occur on W4 but could occur on W5 and W6 because they would be spaced at least by one warp thread W4. This spacing concept applies whether the next lock is formed by the same fill thread F4 or by another fill thread above or below F4. For any particular fill thread the frequency of lock elements would be between about four to fifty warps but would be at least four warps apart. As regards the fill threads, the locks on adjacent fill threads would have at least three fill threads between those which include locks. Preferably there would be between four and sixteen fills between those with locks. Finally in the transverse or fill direction, any two locks created by two separate but successive fills would be separated by at least one fill that did not have locks.

Figure 7:
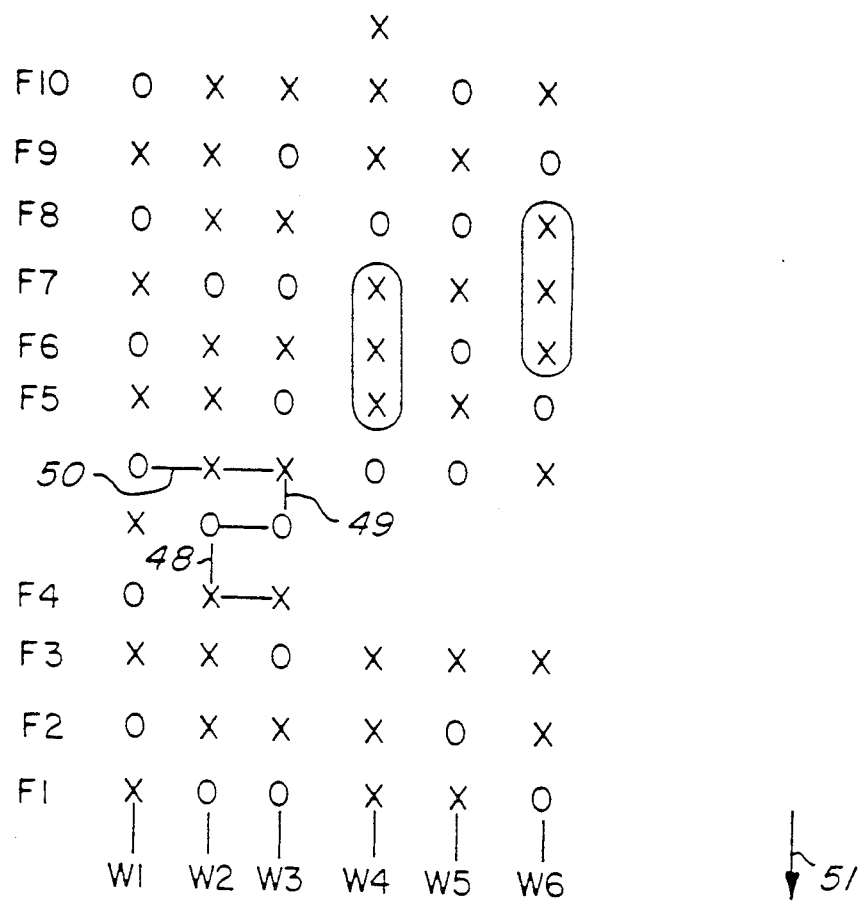
FIG. 7 is a fragmentary schematic plan view showing a lock stitch in a 1/1, 3/1 plain twill weave pattern where each successive 3/1 twill is advanced by one pick.

FIG. 7 shows a 1/1, 3/1 plain, twill weave pattern where the twills on successive warp threads are advanced by one fill thread relative to the twill on the previous warp. This means for example, that the twill is "over three consecutive fills" as indicated where W4 is over F5, F6 and F7. Note that the next consecutive twill warp thread W6 has a twill grouping of 3X's at F6, F7 and F8. Thus, the three X's group at F6-F8 is advanced by one fill from W4's grouping at F5-F7. This kind of advancement of the twill creates a well known diagonal weave pattern. In this drawing the lock stitches are formed by F4 which is shown in a direction from right to left. The lock stitch begins its first reversal where F4 intersects with W2 at reference numeral 48; then the lock stitch goes backward to W3 where it reverses again at 49, and then continues in the direction of reference 50 where it continues to complete that stroke of the shuttle with the fabric then being beaten and moved in the direction of the take-up roll indicated by arrow 51 in FIG. 7.

FIG. 8 is similar to FIG. 7 except that each twill grouping is advanced by two fill threads instead of one. For example warp thread W4 has a group of three Xs at F3, F4, and F5, as contrasted with W6 which has a group of three Xs at F5, F6, and F7, the lead X at F7 being two fills above the lead X of the W4 group which is at F5. In FIG. 8 the lock stitch occurs when F3 reverses about W3 as indicated by reference number 52, then it reverses again at W2 as indicated by reference number 53, and then it continues in the direction of reference number 54 to complete the stroke of that shuttle.

Figure 9:
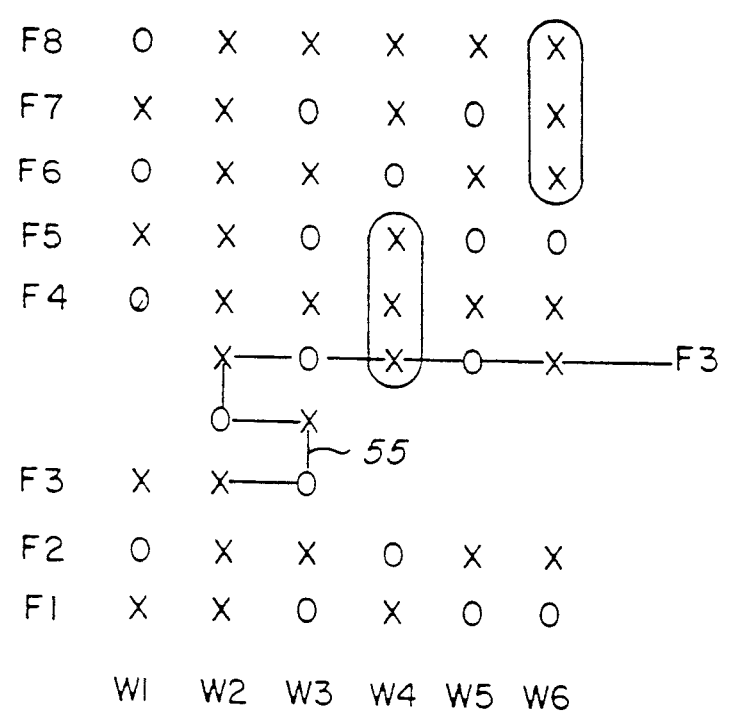

FIG. 9 is similar to FIGS. 7 and 8 except that the 1/1, 3/1 plain, twill weave has the twill pattern of three Xs advanced by three fills instead of by one or two fill threads as in FIGS. 7 and 8 respectively. This is evident, for example, as the three Xs on W6 occur at F6, F7, and F8 as compared to the three X group for W4 which occurs at F3, F4, and F5.

As before, the lock stitch indicated by reference 55 in FIG. 9 is positioned to engage two adjacent warp threads. Each lock element as generally described herein, could be a double reverse as shown about a single warp as opposed to the lock stitch about two adjacent warps which are shown in FIGS. 6 through 9. Also, the lock could wrap around a collection of three warps, however, it is preferred not to wrap around more than four because the fabric could then become pinched.

Figure 10:
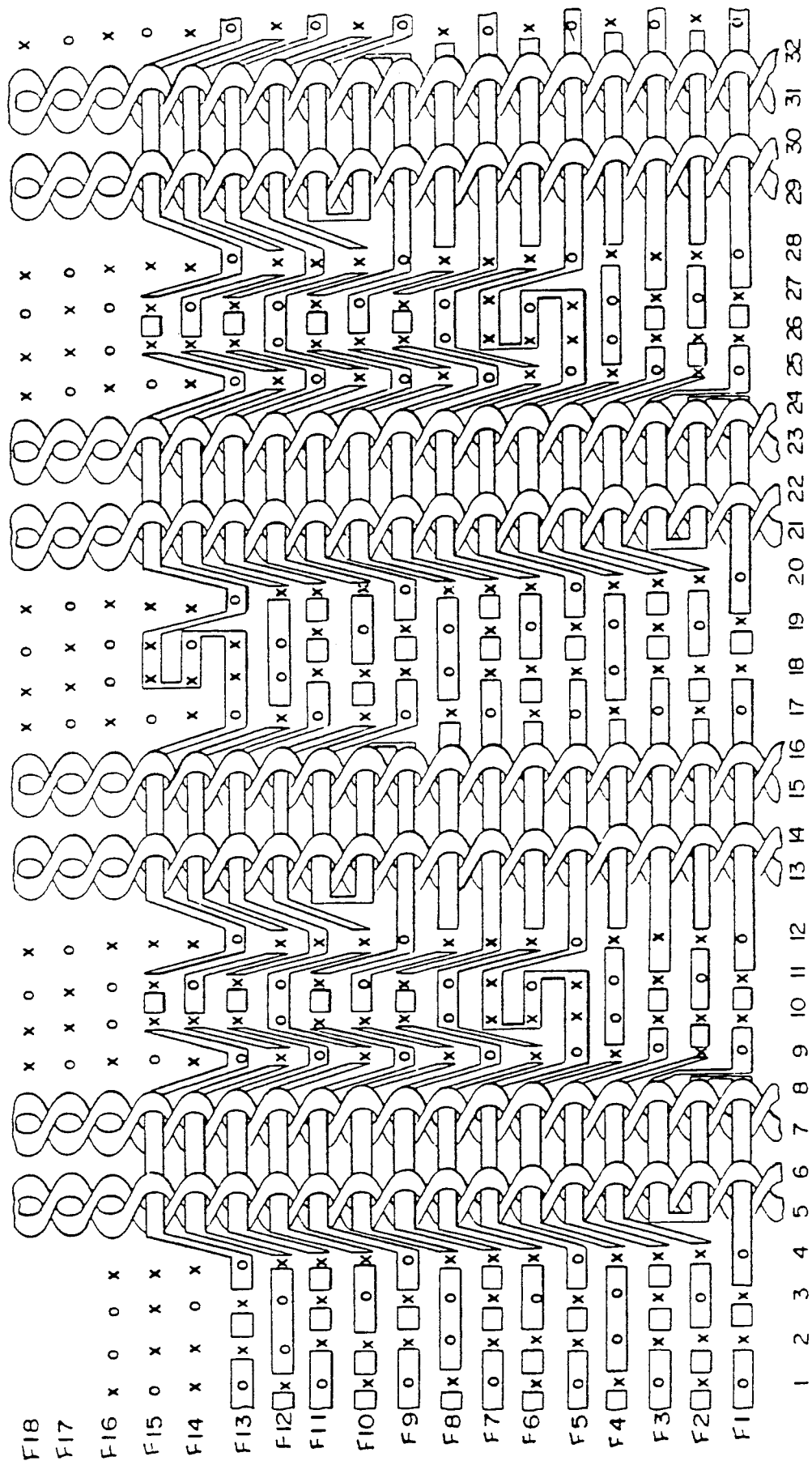
FIG. 10 is a fragmentary schematic plan view in enlarged scale showing a lock stitch in a 1/1, 3/1, 1/1, 3/1, plain, regular twill double leno weave pattern where each successive 3/1 twill is advanced by one pick.

FIG. 10 shows a fragment in enlarged scale of a weave pattern comprising a 1/1, 3/1, 1/1, 3/1, double leno weave, wherein the first four warp threads are woven as plain, twill, plain, twill and the next four warp threads are formed as two lenos or a double leno set. This particular arrangement has been described in applicant's copending application. As before, X's and O's indicate where a warp thread extends "over" and "under" respectively a fill thread. In FIG. 10, this basic weave has been modified to include a series of lock elements of the type previously described herein. The first lock element occurs with fill thread F1 as it traverses through the double lenos formed by warp threads W5, W6, W7, and W8. This fill creates another lock element farther to the right in the weave with warp threads W21-W24. Now, move upward to fill thread F5 which is four fill lines above the previous locking fill thread F1. F5 goes to the right until it locks on W11 and reverses to W10 and then continues until it locks on a plain and twill warp threads W27 and W26. The lock by F5 at warp W10 and W11 is spaced to the right of the previous lock by at least one warp element W9. The next locking fill thread is F9 which locks when it engages the warp threads W13 through W16 of that double leno set and continues to the right. The next locking fill thread is four more threads up at F13 which locks on warp threads W18 and W19 as seen. Again, this locking element is spaced by one warp thread W17 in the transverse direction from the previous locking element at W13, W14, W15, and W16.

The previously-described lock element formed by F1 created a triple layer (i.e., two extra) as it reversed through W5–W8. The F5 thread would normally be four threads up from F1; however, in the vicinity of W5–W8, the F5 thread will be bumped up two extra to line "F7" because of the earlier lock element. Such axial bulges would cause undesirable irregularities in the weave pattern; however, the lock elements are distributed transversely, so that the "bulges" occur at generally uniform intervals, the average fill thread thus "sees" a generally regular pattern of bumps (bulges) and thus "lies" generally flat or horizontal.

In the weaving process a comb beats successive fill layers, moving the woven fabric forward. Each lock stitch becomes embedded in the matrix, the distribution of lock elements being such that at almost any location no more than a few threads can be exposed without a lock element to prevent fraying. In FIG. 10 only a relative number of lock elements is used, because the lenos provide an independent locking means.

Figure 11:
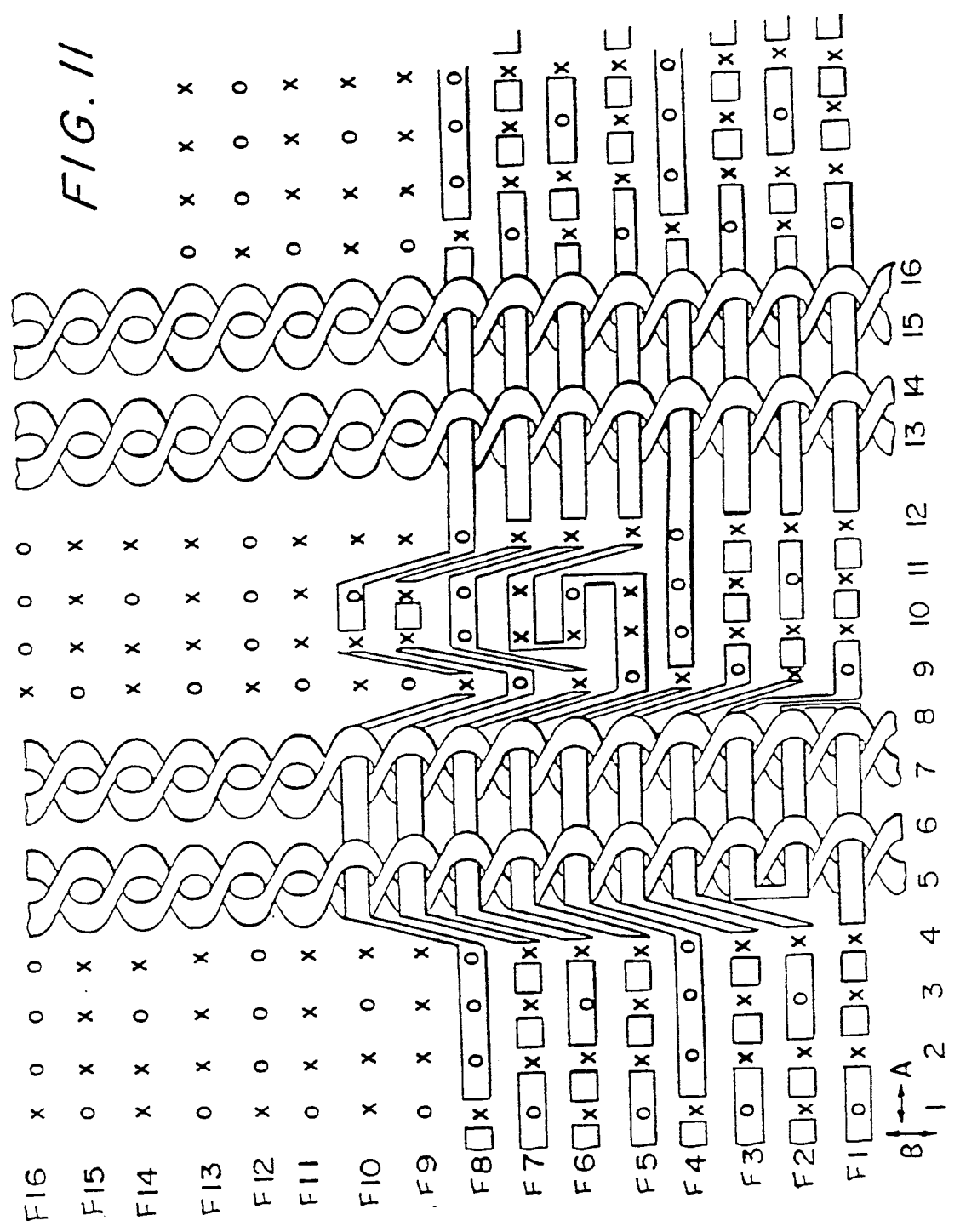

FIG. 11 is generally similar to FIG. 10 except that the twill groupings of three X's on any particular warp thread are parallel and the same as (and do not advance relative to) the three X group on the previous and subsequent warp threads. More particularly note W2 has a group of three X's at F5, F6, and F7, and W4 has three X's also at F5, F6, and F7. Nevertheless, there is a lock element by F1 as it traverses the double leno set at W5, W6, W7, and W8; and four fill threads up at F5 there is a similar lock element where that thread engages warp threads W10 and W11 which are adjacent plain and twill threads.

The above-described preferred embodiments are merely suggestive of many other possible configurations and arrangements that are possible within the spirit and scope of the invention disclosed herein and the claims appended hereto. More specifically, the new lock weave element or stitch can be applied to many different weave patterns shown and not shown where some variety of warp and fill threads are used. As stated earlier, the lock may engage and wrap around a single warp thread, or around two or more adjacent warp threads. The distribution or frequency of these lock elements throughout the weave may vary greatly in both the warp and the fill directions and as relates to lock elements per fill thread or per warp thread, etc. Apparatus other than the named types of looms may be used, and of course many types of yarns may be used. The resulting vascular grafts may comprise a straight cylinder as seen in FIG. 1 or a bifurcated cylinder as seen in FIG. 2, or other shape of tube.

We claim:

1. A vascular graft prosthesis comprising a tube formed of woven fabric and attachable into a vascular system for conveyance of blood therethrough, the fabric comprising a weave having a plurality of warp threads running in the axial or warp direction of the tube and a plurality of standard fill threads running in a direction transverse to said axial direction, the improvement in combination therewith of a plurality of lock weave elements for reducing fraying when said fabric is cut, each lock weave element formed by a portion of one of said standard fill threads woven in an initial fill direction and transversing two adjacent first and second of said warp threads, said portion looped about said second warp thread and extending back in a direction opposite of said initial fill direction traversing said second and first warp threads, said portion then looped about said first warp thread and extending in said initial fill direction and traversing said first and second warp threads, said portion then continuing in said initial fill direction as a standard fill thread in said weave.

2. A vascular graft prosthesis according to claim 1 wherein said weave comprises warp and fill threads woven in a 1/1 plain pattern weave, said lock weave elements formed by portions of fill threads therein looped about warp threads therein.

3. A vascular graft prosthesis according to claim 1 wherein said weave comprises warp and fill threads woven in a 1/1, 3/1 pattern weave, said lock weave elements formed by portions of fill threads therein looped about warp threads therein.

4. A vascular graft prosthesis according to claim 1 wherein said weave comprises warp and fill threads woven in a 1/1, 3/1, 1/1, 3/1, double leno pattern weave, said lock weave elements formed by portions of fill threads therein looped about warp threads therein.

5. A vascular graft according to claim 1 wherein said lock weave elements are distributed such that for any single fill thread the lock weave elements looped about warp threads are separated by at least four consecutive warp threads without lock weave elements formed by that fill thread.

6. A vascular graft according to claim 1 wherein said lock weave elements are distributed such that successive fill threads in the axial direction that have lock weave elements are separated by at least three consecutive fill threads that do not have lock weave elements.

7. A vascular graft according to claim 1 wherein said lock weave elements are distributed such that successive lock weave elements in said transverse direction, formed by successive fill threads, are separated by at least one warp thread.

8. A vascular graft according to claim 1 wherein said lock weave elements are distributed such that for any single fill thread, the lock weave elements looped about warp threads are separated by at least four consecutive warp threads without lock weave elements therein, and said lock weave elements are distributed wherein successive fill threads in the axial direction that have lock weave elements are separated by at least three consecutive fill threads that do not have lock weave elements, and successive lock weave elements in the transverse direction formed by successive fill threads are separated by at least one warp thread.

9. A vascular graft according to claim 1 wherein the portion of said fill thread forming each of said lock elements traverses over both warp threads in one of said fill and opposite fill directions and traverses under both warp threads in the other of said fill and opposite fill directions.

10. A vascular graft according to claim 1 comprising a tube having a primary tubular portion having opposite ends, a bore therethrough of first cross-sectional area, one of said ends being bifurcated and forming two smaller tubular portions each of which has cross-sectional area about half of said first cross-sectional area, the bores of said smaller tubular portions being in communication with the bore of said primary tubular portion.

11. A vascular graft prosthesis comprising a tube formed of woven fabric and attachable into a vascular system for conveyance of blood therethrough, the fabric comprising a weave having a plurality of warp threads running in the axial or warp direction of the tube and a plurality of standard fill threads running in a direction transverse to said axial direction, the improvement in combination therewith of a plurality of lock weave elements for reducing fraying when said fabric is cut, each lock weave element formed by a portion of one of said standard fill threads woven in an initial fill direction and traversing at least two adjacent warp threads, the first and last of said warp threads in the transverse direction being designated first and last warp threads, said portion looped about said last warp thread and extending back in a direction opposite of said initial fill direction traversing said at least two warp threads, said portion then looped about said first warp thread and extending in said initial fill direction and traversing said at least two warp threads, said portion then continuing in said initial fill direction as a standard fill thread in said weave.

12. A vascular graft according to claim 1 wherein said warp and fill threads comprise texturized 64 denier/144 filament polyesther.

13. A vascular graft according to claim 1 wherein said warp and fill threads comprise texturized 75 denier/72 filament polyesther.

14. A vascular graft according to claim 1 wherein said weave pattern comprises warp threads in the range of 140 to 170 threads per inch and said fill threads in the range of 60 to 80 threads per inch.

15. A vascular graft according to claim 1 wherein said fabric has a generally flat interior surface and a velour loop exterior surface for receiving tissue ingrowth.

16. A vascular graft according to claim 12 wherein each of said filaments comprises polyethylene terephthalate weighing less than 1.0 gram per 9000 meters.

* * * * *